United States Patent
Munson et al.

(10) Patent No.: US 6,977,299 B2
(45) Date of Patent: Dec. 20, 2005

(54) METHOD FOR MAKING ACYLAMIDES BY SYNTHESIZING AND ACYLATING BENZOXAZINES

(75) Inventors: Robert Eugene Munson, deceased, late of Baton Rouge, LA (US); by Catherine Munson, legal representative, Baton Rouge, LA (US); Michael Allen Oliver, Daphne, AL (US); Heinz Peter Schwemlein, Mobile, AL (US)

(73) Assignee: Syngenta Crop Protection, Inc., Greensboro, NC (US)

( * ) Notice: Subject to any disclaimer, the term of this patent is extended or adjusted under 35 U.S.C. 154(b) by 348 days.

(21) Appl. No.: 10/296,563

(22) PCT Filed: May 21, 2001

(86) PCT No.: PCT/EP01/05835

§ 371 (c)(1),
(2), (4) Date: May 6, 2003

(87) PCT Pub. No.: WO01/90088

PCT Pub. Date: Nov. 29, 2001

(65) Prior Publication Data

US 2004/0044206 A1   Mar. 4, 2004

Related U.S. Application Data

(60) Provisional application No. 60/325,769, filed on May 23, 2000.

(51) Int. Cl.$^7$ ........................................... C07D 265/36
(52) U.S. Cl. ..................................................... 544/105
(58) Field of Search ........................................ 544/105

(56) References Cited

U.S. PATENT DOCUMENTS

| 2,381,071 A | 8/1945 | McNally et al. |
| 2,381,935 A | 8/1945 | Strain et al. |
| 4,618,361 A | 10/1986 | Moser |
| 5,977,167 A * | 11/1999 | Koga et al. ................. 514/456 |

OTHER PUBLICATIONS

Fujimoto et al., "Preparation of benzoxazine derivatives as intermediates for bactericides", Chemical Abstracts, vol. 116, No. 13, 1992.
Fukushima et al., "Preparation of 6-amino-7-fluoro-2H-1, 4-benzoxazin-3(4H)-o ne as intermediate for herbicides", Chemical Abstracts, vol. 119, No. 15, 1993.

* cited by examiner

Primary Examiner—Joseph K. McKane
Assistant Examiner—Andrew B. Freistein
(74) Attorney, Agent, or Firm—Rose M. Allen

(57) ABSTRACT

A method is provided for synthesizing acylamides, useful as protectant for cultivated plants. A benzoxazine, such as 3,4-dihydro-3-methyl-2H-1,4-benzoxazine, is made in a stepwise manner by initially forming an o-nitrophenoxyketone by reacting a haloketone and a nitrophenol. The o-nitrophenoxyketone is hydrogenated to form the corresponding benzoxazine, which is thereafter acylated with an acylhalide to produce the acylamide, such as 4-dichloroacetyl-3,4-dichloroacetyl-3,4-dihydro-3-methyl-2H-1,4-benzoxazine.

22 Claims, No Drawings

METHOD FOR MAKING ACYLAMIDES BY SYNTHESIZING AND ACYLATING BENZOXAZINES

This application is a 371 of PCT/EP01/05835 filed May 21, 2001, which claims benefit of 60/325,769, filed May 23, 2000.

BACKGROUND OF THE INVENTION

1. Field of the Invention

The present invention relates to a method for making acylamides useful as protectants for cultivated plants against the phytotoxic action of herbicides. More particularly, the present invention relates to a method for making acylamides starting with the initial synthesis of an o-nitrophenoxyketone from an o-nitrophenol and a haloketone. The o-nitrophenoxyketone is then hydrogenated to produce a benzoxazine, which is thereafter acylated to form the desired acylamide.

2. Discussion of the Prior Art

Some of the acylamides which can be made in accordance with the method of the present invention are shown by Moser in U.S. Pat. No. 4,618,361. An acylhalide is reacted with an aromatic amine in the presence of an acid binding agent.

The term "acylamide" as used in the description of the present invention, includes compounds shown within the following formula:

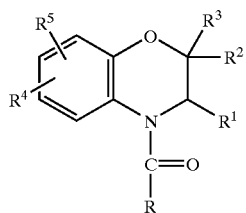

(1)

where R is a $C_{(1-8)}$ monovalent organo functional radical, $R^1$ is a $C_{(1-8)}$ monovalent radical selected from the group consisting of, alkyl and alkoxyalkyl, and $R^2$–$R^5$ are $C_{(1-8)}$ monovalent radicals which can be the same or different, and are selected from the group consisting of hydrogen, alkyl and alkoxyalkyl.

Acylamides included within formula (1), can be synthesized by acylating a benzoxazine in an aromatic hydrocarbon solvent as shown by the following equation:

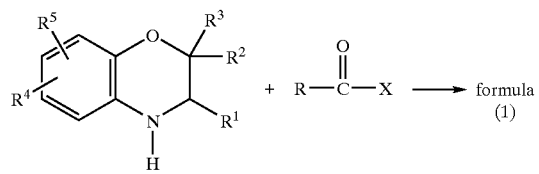

where $R$–$R^5$ are as previously defined and X is a halogen radical.

The formation of benzoxazines, such as 3,4-dihydro-3-methyl-2H-1,4-benzoxazine, can involve the initial synthesis and hydrogenation of a nitrophenoxyketone. For example, Strain et al. U.S. Pat. No. 2,381,935, shows the hydrogenation of o-nitrophenoxyacetone in an autoclave using a Raney nickel catalyst and methanol as a solvent to form a 3-methylbenzoxazine. However, a satisfactory synthesis for the o-nitrophenoxyacetone intermediate used in making the 3-methylbenzoxazine is not set forth by Strain et al.

Although a synthesis for the o-nitrophenoxyacetone intermediate used by Strain et al. is not reported, a procedure for making a phenoxyacetone is shown by H. Meerwein, Houben-Weill, Band 8—Saurstoffverindugen on page 57, by effecting reaction between phenol and monochloroacetone in the presence of potassium carbonate and sodium iodide. While a satisfactory yield of the phenoxyacetone is indicated, a strong solvent, such as a ketone, is used to solubilize the sodium iodide catalyst. Experience has shown that if sodium iodide is used as the catalyst to produce the phenoxyketone, further purification such as recrystallization is required. Otherwise catalyst poisoning can result during the hydrogenation step in the synthesis of the benzoxazine. As a consequence an excessive amount of waste can be generated.

In addition, as shown, for example, in Chemical Abstracts 102: 6171c and 103: 178335w (1985), and 106: 34646n and 106: 175898h (1987), phase transfer catalysts (PTC), such as tetrabutylammoniumbromide, have been used to facilitate the synthesis of ether related materials, such as acridine ethers, and aryloxy derivatives. Solvents such as toluene, aprotic solvents, or acetonitrile, have been found to be effective in the presence of $K_2CO_3$, or NaOH.

While some methods are shown to make acylamides of formula (1) by acylating a benzoxazine, improved procedures are constantly being evaluated for synthesizing benzoxazines, as well as precursors to benzoxazines, such as the corresponding nitroaryloxyketone, for example a nitrophenoxyacetone.

SUMMARY OF THE INVENTION

The present invention is based on the discovery that an o-nitrophenoxyketone having the formula,

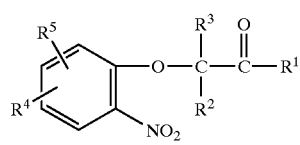

(2)

can be synthesized in an aromatic hydrocarbon solvent, such as toluene, in place of a ketone solvent. The synthesis of the o-nitrophenoxyketone from an o-nitrophenol and a haloketone can be effected in an aromatic organic solvent, such as toluene, in place of a ketone solvent by employing a phase transfer catalyst and an effective amount of an alkali metal halide, for example, an alkali metal bromide. The synthesis of the o-nitro-phenoxyketone is as shown by the following equation:

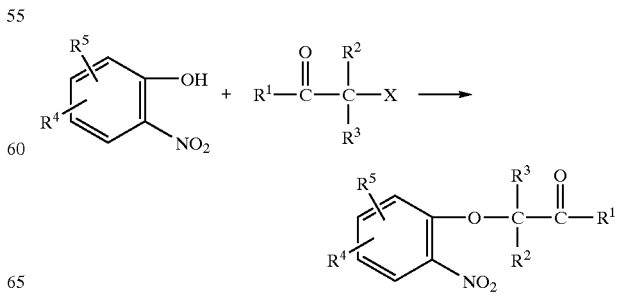

where X, $R^1$–$R^5$ are as previously defined. The synthesis requires using a sufficient amount an acid acceptor, such as an alkali metal carbonate or bicarbonate. Alkali metal bicarbonate acid acceptor is preferred. It has been further found that by switching from a ketone solvent to an aromatic hydrocarbon solvent during the o-nitrophenoxyketone synthesis, a substantial reduction can be realized in the total waste stream which is generated. In addition, by avoiding the use of a ketone solvent, the recrystallization and salt filtration steps also can be eliminated.

Further, the use of a mixture of an aromatic hydrocarbon solvent and an alcohol solvent also has been found to be beneficial for the subsequent reduction step (used to prepare a benzoxazine product). The observed benefits are in terms of reduced by-product formation, improved o-nitrophenoxyketone feed rates and catalyst recovery.

STATEMENT OF THE INVENTION

There is provided by the present invention, a method for making an acylamide of formula (1), comprising the steps of:

(a) effecting reaction in an aromatic organic solvent between an o-nitrophenol and a haloketone in the presence of an acid acceptor, and a catalytic amount of an alkali metal halide and a phase transfer catalyst to form an o-nitrophenoxyketone of formula (2), (b) hydrogenating the o-nitrophenoxyketone of (a) in the presence of an effective amount of a hydrogenation catalyst to produce a benzoxazine of the formula,

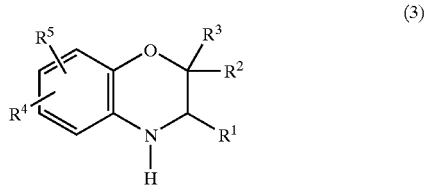

(3)

and, (c) acylating the benzoxazine of (b) with acylhalide having the formula,

(4)

in the presence of an acid acceptor, where R–$R^5$ and X are as previously defined.

DETAILED DESCRIPTION OF THE PRESENT INVENTION

Organofunctional radicals included within R, are for example, $C_{(1-8)}$ organic radicals, such as polyhaloalkyl, for example, dichloromethyl, trichloroethyl; polyhaloalkenyl, and cyanoalky such as cyanoethyl, while R is preferably polyhaloalkyl, such as $(Cl)_2CH$—. Radicals included within $R^1$–$R^5$, are radicals which can be the same or different, and are selected from the group consisting of hydrogen, $C_{(1-8)}$ alkyl, such as methyl, ethyl, propyl, and butyl; alkoxyalkyl, such as methoxyethyl, ethoxyethyl, and propoxybutyl.

In the practice of the first step of the method of the present invention, the o-nitrophenoxyketone can be made by agitating a mixture comprising an o-nitrophenol and a haloalkylketone, such as chloroacetone, or acetylmethylchloride, at a temperature of about 50° C. to about 100° C., and preferably about 55° C. to about 85° C. Reaction can be effected in the presence of an aromatic organic solvent, up to about 0.5 moles of water, per mole of o-nitrophenol, and an effective amount of an acid acceptor, phase transfer catalyst, and an alkali metal halide.

Suitable aromatic organic solvents are for example $C_{(6-10)}$ aromatic hydrocarbon and halogenated hydrocarbon solvents, such as benzene, chlorobenzene, toluene, which is preferred, and xylene. Phase transfer catalysts which can be used are for example, quaternery ammonium and phosphonium salts, such as $(R^6)_4N^+$, and $(R^7)_4P^+$, where $R^6$, and $R^7$ are preferably, organic groups, such as $C_{(1-4)}$ alkyl groups. Among the preferred phase transfer catalysts, there are included tributylmethylammonium chloride, and tributylmethylammonium bromide.

Acid acceptors which can be used are preferably alkali metal carbonates or bicarbonates, such as sodium or potassium carbonate or bicarbonate.

Reaction times can vary in the range of 1 to 14 hours, depending upon such factors as temperature, amount of haloalkylketone, water, and amounts and relative ratios of alkali metal halide catalyst and phase transfer catalyst. During work up, water can be added to the reaction mixture at a temperature of from about 40° C. to 75° C., and the pH of the mixture can be adjusted to a range within 3–7.0 with addition of a mineral acid, such as HCl. The phases can be separated, and a salt solution, such as an NaCl solution, can be added to the organic phase. The phases can be separated again and the solvent and volatile impurities can be removed from the organic phase by distillation at 45° C. to 85° C. under reduced pressure to recover the o-nitrophenoxyketone. In particular instances, additional recrystallization of the o-nitrophenoxyketone from an alkanol such as isopropanol has been found desirable to minimize any adverse effects on the performance of the hydrogenation catalyst in the reduction step. However, by maintaining optimum reaction conditions, including catalyst proportions, it has been found that a reduction in by product level can be achieved, which can avoid the need to recrystallize the o-nitrophenoxyketone.

In preparing the o-nitrophenoxyketone, it is preferred to add the o-nitrophenol and the haloalkylketone and an acid acceptor, such as an alkali metal bicarbonate, in the presence of the alkali metal halide and aromatic organic solvent. There can be used, per mole of o-nitrophenol, 1.03 to 1.06 moles of haloalkylketone, about 1.0 to about 1.2 moles of acid acceptor, 0.04 to 0.15 moles of alkali metal halide, and 0.01 to 0.06 moles of phase transfer catalyst (PTC). A molar ratio of alkali metal halide/PTC having a value of 2 to 6, and more preferably 2.5 to 6, also can be used.

In the practice of the second step of the method of the present invention, the o-nitrophenoxyketone can be converted to a benzoxazine by hydrogenation in a reactor. Hydrogenation can be effected in a semibatchwise or continuous manner, by adding a solution of the o-nitrophenoxyketone in an aromatic organic solvent, such as toluene, to an agitated slurry of the hydrogenation catalyst in an aromatic organic solvent. The use of a cosolvent, such as a $C_{(1-8)}$ alkanol, and particularly methanol or isopropanol, which is preferred, has been found to minimize the formation of by-products, such as the corresponding benzoxazine "dimers" (several). The presence of an effective amount of a $C_{(1-8)}$ alkanol also has been found to improve the flowability and filtration characteristics of the catalyst slurry. As a result, the recovery and recycling of the catalyst is improved. Based on volume %, a proportion of 20–80% o-nitrophenoxyketone and 80–20% of solvent is preferred. A weight ratio of about 11 to 17 parts of o-nitrophenoxyketone, per part of hydrogenation catalyst will provide effective results. A 95/5 to 50/50 cosolvent weight ratio of the aromatic organic solvent to alkanol can be used.

A reaction temperature of 50–90° C. can be used, with a preferred temperature of about 60° C. along with pressures of about 60 psig to 230 psig. In instances where the o-nitrophenoxyketone is fed continuously into the reactor, adjustment to a slower feed rate can reduce dimer formation. While platinum is the preferred catalyst, other Platinum Group Metal (PGM) catalysts, such as ruthenium, rhodium, palladium, osmium, iridium are effective. An effective amount of PGM catalyst is 650 to 5000 ppm of PGM catalyst, and preferably 1300 to 4400 ppm per reaction slurry amount. Hydrogenation reaction time can vary between about 2.5 to about 14 hours.

The acylation of the benzoxazine in the third step of the method of the present invention can be achieved by effecting reaction between the acylhalide and the benzoxazine in an aromatic organic solvent and in the presence of an acid acceptor. Conditions used in the acylation of the benzoxazine are substantially the same as shown in Moser, U.S. Pat. No. 4,618,361, which is incorporated by reference herein.

Suitable acid acceptors include alkali metal hydroxides, such as sodium hydroxide, while alkali metal carbonates and bicarbonates are preferred.

In order that those skilled in the art will be better able to practice the present invention, the following examples are given by way of illustration, and not by way of limitation. All parts are by weight unless otherwise indicated.

EXAMPLE 1 o-nitrophenoxyacetone

The o-nitrophenoxyacetone is prepared by heating with agitation for five hours at about 65° C. a mixture which consists of 421.6 g (3.006 moles) of o-nitrophenol, 297.8 g (3.09 moles) of chloroacetone, 37.2 g (96%, 0.3615 moles) of sodium bromide, 277.2 g (3.3 moles) of sodium bicarbonate, 21.8 g (0.0647 moles) of aqueous tributylmethylammonium chloride (TBMAC), and 829 g of toluene. There is then added 9.0 g (0.093 mole) of additional chloroacetone to the mixture which is further heated at 65° C. for 2.5 hours (note, sample analysis indicated that the reaction was complete after 1.5 hours). There is then added, 570 g of water and the pH of the mixture is adjusted to 6.5–7 at 55° C. to 60° C. upon addition of 55 g of a 10% HCl solution. The phases are allowed to separate and the aqueous phase is removed.

There is added 600 g of a 5% NaCl solution to the organic phase and the resulting mixtures is vigorously agitated at 55° C. to 60° C. Upon separation of the phases, the organic phase is transferred to a rotary evaporator; volatiles are removed under vacuum at 65–70° C. Sufficient toluene is used during the solvent strip to provide substantially complete chloroacetone separation. There is obtained 580.1 g of o-nitrophenoxyacetone which is a 95.9% yield relative to o-nitrophenol.

EXAMPLE 2

3,4-dihydro-3-methyl-2H-1,4-benzoxazine (3-MBA)

A previously filtered mixture of 273.2 g (97%, 1.359 mole) of o-nitrophenoxyacetone, 178 g of toluene, and 44 g of isopropanol at 55–60° C. is added over a three hour period to a Parr reactor under 200 psig of hydrogen pressure and containing an agitated mixture of 85.5 g of a water wet 5% platinum on carbon catalyst (24.1 g on dry basis, Engelhart), 168 g of toluene, and 42 g of isopropanol at 55–60° C. During the addition, the hydrogen pressure and the temperature are maintained at 200 psig and 60° C., respectively. At the end of the addition, the conditions of the reactor are maintained for an additional 60 minutes.

The pressure of the Parr reactor is initially relieved and then is opened. The cooling coils and agitator shaft are washed with toluene/isopropanol; the warm slurry is filtered under 7 to 15 psig pressure. The catalyst is filtered and washed with 140 g of toluene/isopropanol and 280 of water. The resulting organic phase is stripped under vacuum in a rotary evaporator to yield 193.5 g of the desired product (97.7% yield).

EXAMPLE 3

(±)-4-dichloroacetyl-3,4-dihydro-3-methyl-2H-1,4-benzoxazine (benoxacor)

a) o-Nitrophenoxyacetone (o-NPA)

The following materials are combined in a 1000 gallon vessel and heated at 65° C. for 6–8 hours: 499.0 kg (1.000 mole equiv.) of o-Nitrophenol (o-NP, 99%, 3.551 kg-moles), 359.7 kg (1.05 mole equiv.) of chloroacetone (CA, 96%, 3.733 kg-moles), 45.4 kg (0.124 mole equiv.) of sodium bromide (0.441 kg-moles), 328.9 kg (1.102 mole equiv.) of sodium bicarbonate (3.915 kg-moles), 27.2 kg (0.023 mole equiv.) of aqueous tributylmethylammonium chloride (TBMAC, 70%, 0.081 kg-moles), and 989 kg of toluene. The reaction is checked for completion and a trim charge of chloroacetone is added if necessary. Then 682 kg of water are added at 60° C. and the pH of the reaction mixture is adjusted to pH 6.5 –7.0 at 55 to 60° C. (about 66 kg of 10% HCl). The phases are separated and the heavier aqueous phase is removed. A 5–15% NaCl solution (725 kg) is added to the organic phase, the mixture is agitated at 55 to 60° C. and the phases are separated again by decantation. The remaining organic phase of crude o-NPA is vacuum stripped at 65–75° C. to remove toluene and volatile impurities. Toluene (about 70 kg) is added towards the end of the vacuum strip and stripped off again to improve the removal of volatile impurities. About 691 kg of crude o-NPA (96.9% assay, 3.428 kg-moles, 96.5% yield rel. o-NP) are obtained. Finally 339 kg of a toluene/isopropanol (8:2) mixture is added at 55–65° C. to the crude o-NPA melt to obtain approximately a 65% o-NPA solution. This solution is transferred to a hold vessel where it is held at 65° C. for step b.

b) 3,4-dihydro-3-methylbenzomorpholine (3-MBA)

The 65% solution (1030 kg) of o-NPA (3.428 kg-moles, 1.000 mole-equiv.) in 8:2 toluene/Isopropanol at about 65° C. from a) is added over a period of about 5 hours to a slurry of 42 kg of a 5% platinum on carbon catalyst (Engelhart), 42 kg of water, 436 kg toluene/isopropanol (8:2) in a 500 gallon vessel, while pressurized with hydrogen gas to 80–200 psig (31.1 kg, 15.54 kg-moles, 4.53 mole-equiv.) at a temperature of 60–80° C. The feed tank is rinsed with about 50 kg of a 8:2 toluene/isopropanol mixture to the hydrogenation vessel and the hydrogenation is continued for another 0.5 hours. The reaction mixture is filtered and the catalyst is washed with 252 kg of a 8:2 toluene/isopropanol mixture at 60° C. followed by 502 kg of water at 60° C. The resulting combined two phase filtrate can be treated with 0.5–7 kg of 93% sulfuric acid to remove impurities. The bottom aqueous layer is removed and the top 3-MBA containing organic layer is concentrated by atmospheric distillation to obtain approximately a 50% 3-MBA in toluene solution (959 kg total, 479 kg 3-MBA, 3.209 kg-moles, 93.6% yield rel. o-NPA) for step c. The catalyst on the filter is washed further with 753 kg of 60° C. hot methanol followed by 502 kg of water and is then flushed back to the reactor with 436 kg of 8:2 toluene/isopropanol).

c) Benoxacor

The about 50% solution of 3-MBA (959 kg total, 479 kg 3-MBA, 3.209 kg-moles) from b) is transferred to a 1000 gallon vessel and 542 kg of water and 14 kg of 75% phosphoric acid are added. A 30% NaOH (3.63 kg-moles) solution (484 kg) and a mixture of 529 kg dichloroacetylchloride (98.6%, 3.538 kg-moles) and 461 kg of toluene are fed simultaneously to the 50% 3-MBA solution. During the feed the pH is maintained between 2.5 and 3.0 and the temperature is ramped from 40 to 80° C. The reaction mixture is held for another hour at 80° C. after the end of the feed to complete the reaction. While holding at 80° C., 5 kg of Celite® is added and the mixture is filtered to remove a rag layer, then the bottom water layer is decanted off. The product is isolated by vacuum distillation of the volatiles and the product melt is drummed out at 110° C. to give 839 kg crude benoxacor (95.0% assay, 797 kg benoxacor, 3.065 kg-moles, 95.5% rel. 3-MBA).

In summary, it is seen that this invention provides a new process for making acylamides. Variations may be made in proportions, procedures and materials without departing from the scope of the invention as defined by the following claims.

What is claimed is:

1. A method for making an acylamide of the formula,

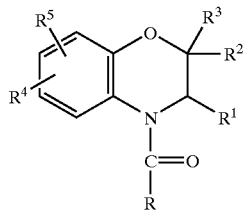

comprising the steps of:
(a) effecting reaction in an aromatic organic solvent between an o-nitrophenol and a haloketone in the presence of an acid acceptor, an effective amount of an alkali metal halide, and a phase transfer catalyst, to form an o-nitrophenoxyketone of the formula,

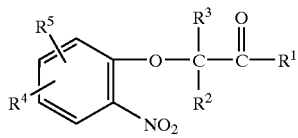

(b) hydrogenating the o-nitrophenoxyketone of (a) in the presence of an effective amount of a hydrogenation catalyst to produce a benzoxazine of the formula,

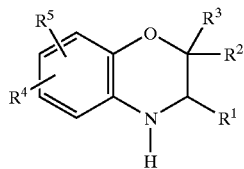

and,
(c) acylating the benzoxazine of (b) with an acylhalide having the formula,

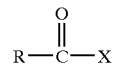

in the presence of an acid acceptor,
wherein R is a $C_{(1-8)}$ monovalent organo functional radical, $R^1$ is a $C_{(1-8)}$ monovalent radical selected from the group consisting of alkyl and alkoxyalkyl, and $R^2$–$R^5$ can be the same or different, and are selected from the group consisting of hydrogen, and $C_{(1-8)}$ monovalent alkyl and alkoxyalkyl radicals, and X is halogen.

2. The method of claim 1, wherein the acylamide is 4-dichloroacetyl-3,4-dihydro-3-methyl-2H-1,4-benzoxazine.

3. The method of claim 1, wherein an alkali metal bicarbonate is used as an acid acceptor during the acylation of the benzoxazine.

4. The method of claim 1, step (c) wherein the acylation of the benzoxazine is effected at a pH of about 4–8.

5. The method of claim 1, step (a), wherein the o-nitrophenoxyketone is the reaction product of chloroacetone and o-nitrophenol.

6. The method of claim 1, step (a), wherein the aromatic organic solvent is toluene.

7. The method of claim 1, step (a), wherein sodium bromide is the alkali metal halide used during the synthesis of the o-nitrophenoxyketone.

8. The method of claim 1, step (a), wherein sodium iodide is the alkali metal halide used during the synthesis of the o-nitrophenoxyketone.

9. The method of claim 1, step (a), wherein the phase-transfer-catalyst is tributylmethylammonium chloride.

10. The method of claim 1, step (a), wherein a reaction temperature of 50–75° C. is used during the synthesis of the o-nitrophenoxyketone.

11. The method of claim 1, step (b), wherein the hydrogenation is effected in the presence of a Platinum Group Metal catalyst.

12. The method of claim 1, step (b), where the hydrogenation is effected in the presence of a platinum catalyst.

13. The method of claim 12, wherein the hydrogenation catalyst is a Pt on carbon.

14. The method of claim 1, where the benzoxazine is a 3-alkyl benzoxazine.

15. The method of claim 1, where the benzoxazine is a 3,4-dihydro-3-methyl-2H-1,4-benzoxazine.

16. The method of claim 1, step (a), where 2.5 to 6 parts of alkali metal halide, per part of phase-transfer catalyst is used during the synthesis of the o-nitrophenoxyacetone.

17. A method for making a 4-dichloroacyl-3,4-dihydro-3-methyl-2H-1,4-benzoxazine, which comprises the steps of:
(a) effecting reaction in toluene between an o-nitrophenol and chloroacetone in the presence of an acid acceptor, a catalytic amount of sodium bromide, and a phase transfer catalyst to form the corresponding o-nitrophenoxyacetone,
(b) hydrogenating the o-nitrophenoxyacetone of (a) to form the corresponding 3,4-dihydro-3-methyl-2H-1,4-benzoxazine, and (c) acylating the 3,4-dihydro-3-methyl-2H-1,4-benzoxazine of (b) with a dichloroacylchloride.

18. A method for making (±)-4-dichloroacetyl-3,4-dihydro-3-methyl-2H-1,4-benzoxazine in accordance with claim 17.

19. A method in accordance with claim 17, wherein the phase transfer catalyst is tributylmethylammonium chloride.

20. A method in accordance with claim 17, wherein the acid acceptor is sodium bicarbonate.

21. A method in accordance with claim 17, wherein the hydrogenation of the o-nitrophenoxyacetone is effected in the presence of an effective amount of a Platinum Group Metal catalyst.

22. A method in accordance with claim 21, wherein the hydrogenation catalyst is platinum on carbon.

* * * * *